United States Patent [19]

Holtkamp, Sr.

[11] Patent Number: Plant 6,604

[45] Date of Patent: Feb. 14, 1989

[54] AFRICAN VIOLET PLANT NAMED MARY

[75] Inventor: Reinhold Holtkamp, Sr., Isselburg, Fed. Rep. of Germany

[73] Assignee: Gessellschaftsvertrag uber die Erfindergeminschaft "Optimara", Rees Haffen, Fed. Rep. of Germany

[21] Appl. No.: 56,411

[22] Filed: Jun. 1, 1987

[51] Int. Cl.[4] ..... A01H 5/00
[52] U.S. Cl. ..... Plt./69
[58] Field of Search ..... Plt./69

[56] References Cited

PUBLICATIONS

Zimmerman, M. W. et al (Ed.) *Sunset House Plants* (p. 79 only) Pub: Sunset Books, Sep. 1983.

*Primary Examiner*—James R. Feyrer
*Attorney, Agent, or Firm*—Foley & Lardner, Schwartz, Jeffery, Schwaab, Mack, Blumenthal & Evans

[57] ABSTRACT

An African violet plant named Mary, characterized by its white flowers with pink center radiating irregularly towards the very delicately frilled edges; tight bouquet about the leaves; strong upright flower stems curving slightly toward the center; profuse flowering; vigorous growth habit; medium green, velvety, round, serrated leaves; and long lasting and non-dropping single flowers.

1 Drawing Sheet

The present invention comprises a new and distinct cultivar of African violet plant, botanically known as *Saintpaulia ionantha,* and hereinafter referred to by the cultivar name Mary.

The new cultivar Mary is a mutation and was discovered by applicant in 1985 in Nashville, Tenn., while growing as a single plant among plants of the parent cultivar Improved Oregon, disclosed in U.S. Plant Pat. No. 5,600. The new cultivar was immediately recognized by its generally white flower color, as compared to the pink flower color of its parent, and was given the selection number M/G 93/XXIII. The parent cultivar Improved Oregon was developed in a breeding program in Isselburg, Federal Republic of Germany from a female parent identified as C165/2X and a male parent identified as F 111 pink frilled.

Asexual reproduction of the new cultivar by leaf cuttings, as performed by me at both Nashville, Tenn. and Haffen, Federal Republic of Germany, has demonstrated that the combination of characteristics as herein disclosed for the new cultivar are firmly fixed and retained through successive generations of asexual reproduction.

Mary has not been observed under all possible environmental conditions. The phenotype may vary significantly with variations in environment such as temperature, light intensity and day length. The following observations, measurements and values describe the new cultivar as grown in 10 cm pots in Haffen, Federal Republic of Germany and Nashville, Tenn. under greenhouse conditions which closely approximate those generally used in commercial practice.

The following traits have been repeatedly observed and are determined to be basic characteristics of Mary which in combination distinguish this African violet as a new and distinct cultivar:

1. Strong upright flower stems curving slightly toward the center.
2. White flowers with pink center radiating irregularly towards the very delicately frilled edges.

3. First flash of flowers appears 9–10 weeks after potting and forms a tight bouquet above the leaves.
4. Long-lasting, non-dropping single flowers.
5. Each plant carries 10–12 upright flower stems, each of which carries 7–9 and more flowers.
6. Profuse flowering.
7. Seed capsule pushes slightly through.
8. Vigorous grower.
9. Plant saleable 10–11 weeks after potting.
10. Medium green, velvety, round leaves, serrated.
11. After maturity, the flowers dry off and remain on the peduncle without becoming infected by botrytis.

The new cultivar is most similar to its parent Improved Oregon. Mary is principally distinguished from Improved Oregon by the color of the flowers.

The accompanying color photographic drawing shows a typical specimen plant of the new cultivar. The colors appearing in the photograph are as true as possible with color illustration of this type.

In the following description, color references are made to the Royal Horticultural Society Colour Chart (RHS), except where general colors of ordinary significance are referred to. Color values were taken under natural light conditions at approximately 2.00 p.m. in Nashville, Tenn. Under cooler growing conditions and more intensive lighting, the pink color becomes more intense.

Botanical clafficication: *Saintpaulia ionantha,* Ramat., cv. Mary.

Propagation: The new cultivar holds its distinguishing characteristics through successive propagations by leaf cuttings and by division of shoots.

Plant: From 7 cm to 9 cm tall when grown in pots, and approximately 25 cm in diameter when fully grown. The growth rate is vigorous.

*Leaves.*—Shape: Round. Diameter: 55–70 mm. Texture: Leather-like. Aspect: Velvety, hairy, slightly shiny, serrated. Ribs and veins: Upper side visible, under side well pronounced, light green, shiny. Color (Upper side): Between 147 A and B; (photograph is darker). Color (under side): Yellow green 147D. Petioles: Strong, upright, light green, hairy.

*Flowers.*—Buds: Ball-shaped, 7–8 mm before opening, light green. Sepals: Five (5) in number, green. Calyx: Funnel-shaped. Aspect: Spear-shaped, hairy. Peduncle: Strong, upright, green, sometimes with light purplish touch, hairy.

*Individual flowers.*—Size: 35–40 mm. Shape: Single violet-shaped, frilled edges. Color (upper side): White with red purple 58A throat; pink to red tinging radiates irregularly from the throat. Color (under side): Slight amounts of pink 65B intensifying toward the center to 65A. Borne: Each of the 10–12 flower stems carries 7–9 and more flowers on strong, upright, wire-like peduncles that are free standing above the leaves. Flowering habit: Flowers 9–10 weeks after potting. Corolla: Very profuse and tight, free standing above the leaves.

*Reproductive organs.*—Stamens: Two (2) in number. Anthers: Two stamens composed of 4 anther cells, seed capsule pushes slightly through. Filaments: 4 mm long, yelowish green. Pollen Color: Yellow 7A. Styles: 6 mm long, light pink, base of ovary light green.

*Roots.*—Normally developed, white when young, turning slightly brownish when older.

Disease resistance: Good.

General observations: Mary is a vigorous grower, with 10–12 flower stems each carrying 7–9 single, violet-shaped flowers. The flowers are white with a pink center and have delicately frilled edges. The medium green, velvety, serrated leaves give the plant a fresh look. The fully developed flower head forms a tight bouquet that is free-standing above the leaves. Approximately 10–11 weeks after potting the plant is saleable. The flowers are long-lasting and non-dropping and the seed capsule pushes slightly through.

I claim:

1. A new and distinct cultivar of African violet named Mary, as described and illustrated, and particularly characterized by its white flowers with pink center radiating irregularly towards the very delicately frilled edges; tight bouquet above the leaves; strong upright flower stems curving slightly toward the center; profuse flowering; vigorous growth habit; medium green, velvety, round, serrated leaves; and long lasting and non-dropping single flowers.

* * * * *

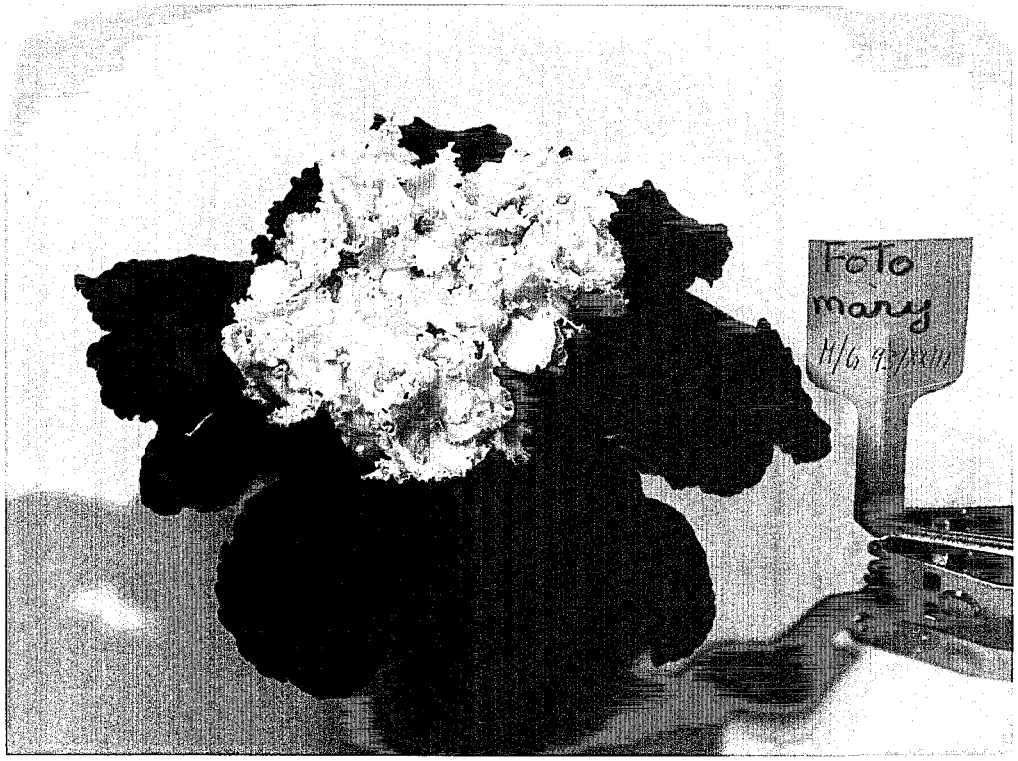
Foto
mary